(12) United States Patent
Salamone et al.

(10) Patent No.: US 7,884,141 B2
(45) Date of Patent: Feb. 8, 2011

(54) BIOMEDICAL DEVICES

(75) Inventors: Joseph C. Salamone, San Antonio, TX (US); Derek A. Schorzman, Cary, NC (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 12/248,202

(22) Filed: Oct. 9, 2008

(65) Prior Publication Data

US 2009/0122260 A1    May 14, 2009

Related U.S. Application Data

(60) Provisional application No. 60/987,801, filed on Nov. 14, 2007.

(51) Int. Cl.
| | | |
|---|---|---|
| G02B 1/04 | (2006.01) | |
| C08G 61/02 | (2006.01) | |
| G02C 7/04 | (2006.01) | |
| C08F 20/68 | (2006.01) | |
| C08F 26/00 | (2006.01) | |

(52) U.S. Cl. ............... 523/106; 351/160 R; 526/311
(58) Field of Classification Search ............... 523/106
See application file for complete search history.

(56) References Cited

U.S. PATENT DOCUMENTS

| | | | |
|---|---|---|---|
| 3,220,960 A | 11/1965 | Wichterle et al. | |
| 3,408,429 A | 10/1968 | Wichterle | |
| 3,660,545 A | 5/1972 | Wichterle | |
| 4,113,224 A | 9/1978 | Clark et al. | |
| 4,136,250 A | 1/1979 | Mueller et al. | |
| 4,153,641 A | 5/1979 | Deichert et al. | |
| 4,163,608 A * | 8/1979 | Neefe ................ 351/160 H | |
| 4,197,266 A | 4/1980 | Clark et al. | |
| 4,208,364 A | 6/1980 | Shepherd | |
| 4,440,918 A | 4/1984 | Rice et al. | |
| 4,555,732 A | 11/1985 | Tuhro | |
| 4,740,533 A | 4/1988 | Su et al. | |
| 4,954,587 A | 9/1990 | Mueller | |
| 4,990,582 A | 2/1991 | Salamone | |
| 4,996,275 A | 2/1991 | Ellis et al. | |
| 5,010,141 A | 4/1991 | Mueller | |
| 5,034,461 A | 7/1991 | Lai et al. | |
| 5,070,215 A | 12/1991 | Bambury et al. | |
| 5,079,319 A | 1/1992 | Mueller | |
| 5,260,000 A | 11/1993 | Nandu et al. | |
| 5,271,875 A | 12/1993 | Appleton et al. | |
| 5,310,779 A | 5/1994 | Lai | |
| 5,321,108 A | 6/1994 | Kunzler et al. | |
| 5,358,995 A | 10/1994 | Lai et al. | |
| 5,374,662 A | 12/1994 | Lai et al. | |
| 5,387,662 A | 2/1995 | Künzler et al. | |
| 5,420,324 A | 5/1995 | Lai et al. | |
| 5,496,871 A | 3/1996 | Lai et al. | |
| 5,539,016 A | 7/1996 | Kunzler et al. | |
| 5,710,302 A | 1/1998 | Künzler et al. | |
| 5,714,557 A | 2/1998 | Künzler et al. | |
| 6,762,264 B2 | 7/2004 | Künzler et al. | |
| 7,078,560 B2 | 7/2006 | Houben et al. | |
| 7,084,188 B2 | 8/2006 | Lai et al. | |
| 7,176,268 B2 | 2/2007 | Lai et al. | |
| 2002/0149740 A1 | 10/2002 | Hopken et al. | |
| 2005/0079470 A1* | 4/2005 | Rutherford et al. ......... 433/226 |
| 2005/0203199 A1* | 9/2005 | Moszner et al. ............. 522/6 |
| 2005/0228065 A1 | 10/2005 | Nicolson et al. | |
| 2005/0281757 A1* | 12/2005 | Ibrahim et al. ............. 424/49 |

FOREIGN PATENT DOCUMENTS

| | | |
|---|---|---|
| EP | 0963761 A | 12/1999 |
| JP | 60178849 | 9/1985 |
| JP | 60178755 | 4/1986 |
| JP | 03179002 A * | 8/1991 |
| WO | WO 96/31792 | 10/1996 |

OTHER PUBLICATIONS

English translation of JP 03-179002 A, Yuasa et al, Aug. 5, 1991.*

\* cited by examiner

*Primary Examiner*—Mark Eashoo
*Assistant Examiner*—David Karst
(74) *Attorney, Agent, or Firm*—John E. Thomas

(57) ABSTRACT

Biomedical devices are provided herein which are formed from a polymerization product of a monomeric mixture comprising (a) one or more esterified aminoalcohol monomers; and (b) one or more biomedical device-forming monomers.

12 Claims, No Drawings

BIOMEDICAL DEVICES

This application claims benefit of provisional patent application No. 60/987,801 filed Nov. 14, 2007 which is incorporated by reference herein.

BACKGROUND OF THE INVENTION

1. Technical Field

The present invention generally relates to biomedical devices, and especially ophthalmic lenses that are intended for direct placement on or in the eye such as contact lenses or intraocular lenses.

2. Description of Related Art

In the field of biomedical devices such as contact lenses, various factors must be considered in order to yield a material that has appropriate characteristics. For example, various physical and chemical properties such as oxygen permeability, wettability, material strength and stability are but a few of the factors that must be carefully balanced to provide a useable contact lens. Since the cornea receives its oxygen supply exclusively from contact with the atmosphere, good oxygen permeability is a critical characteristic for any contact lens material. Wettability is also important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

For example, contact lenses made from silicone materials have been investigated for a number of years. Such materials can generally be subdivided into two major classes, namely hydrogels and non-hydrogels. Hydrogels can absorb and retain water in an equilibrium state whereas non-hydrogels do not absorb appreciable amounts of water. Regardless of their water content, both hydrogel and non-hydrogel silicone contact lenses tend to have relatively hydrophobic, non-wettable surfaces.

By introducing fluorine-containing groups into contact lens polymers, the oxygen permeability can be significantly increased. For example, U.S. Pat. No. 4,996,275 discloses using a mixture of comonomers including the fluorinated compound bis(1,1,1,3,3,3-hexafluoro-2-propyl)itaconate in combination with organosiloxane components. Fluorinating certain polysiloxane materials has been indicated to reduce the accumulation of deposits on contact lenses made from such materials. See, for example, U.S. Pat. Nos. 4,440,918; 4,954,587; 4,990,582; 5,010,141 and 5,079,319. However, fluorinated polymers can suffer from one or more of the following drawbacks: difficult and/or expensive synthetic routes, poor processability, low refractive index, poor wettability, poor optical clarity, poor miscibility with other monomers/reagents and toxicity.

Accordingly, it would be desirable to provide improved biomedical devices such as contact lenses that exhibit suitable physical and chemical properties, e.g., oxygen permeability and wettability, for prolonged contact with the body while also being biocompatible.

SUMMARY OF THE INVENTION

In accordance with one embodiment of the present invention, a biomedical device formed from a polymerization product of a monomeric mixture comprising (a) one or more esterified aminoalcohol monomers of general Formula I:

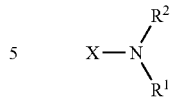

wherein X, $R^1$ and $R^2$ are as defined herein, and (b) one or more biomedical device-forming comonomers.

In accordance with a second embodiment of the present invention, a biomedical device formed from a polymerization product of a monomeric mixture comprising (a) one or more esterified aminoalcohol monomers of general Formula I:

wherein X, $R^1$ and $R^2$ are as defined herein, and (b) one or more siloxy-containing monomers.

In accordance with a third embodiment of the present invention, a contact lens is provided which comprises a polymerization product of a monomeric mixture comprising (a) one or more esterified aminoalcohol monomers of general Formula I:

wherein X, $R^1$ and $R^2$ are as defined herein, and (b) one or more siloxy-containing monomers.

The esterified aminoalcohol monomers for use in the biomedical devices of the present invention, such as in a contact lens polymer formulation, could provide enhanced antimicrobial character to a contact lens, as well as an ability to reduce the accumulation of cationic proteins, such as lysozyme, and the adsorption of cationic antimicrobials. For example, the positive charge of the resulting aminoalcohol-containing polymers at physiological pH could hinder the adsorption of positively charged proteins, such as lysozyme, to a contact lens, as well as low and high molecular weight cationic biocides because of charge repulsion. The alcohol nature of the monomer units could also increase the wettability of the lens. Thus, the resulting lens polymer incorporating the esterified aminoalcohol groups could have improved characteristics, including enhanced surface wettability, enhanced water absorption to a silicone hydrogel, as well as retarding the accumulation of protein deposits, which are usually lysozyme, and retarding the adsorption of positively charged biocides, which can lead to ocular irritation or ocular staining.

DETAILED DESCRIPTION OF THE PREFERRED EMBODIMENTS

The present invention is directed to biomedical devices intended for direct contact with body tissue or body fluid. As used herein, a "biomedical device" is any article that is designed to be used while either in or on mammalian tissues or fluid, and preferably in or on human tissue or fluids. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. The preferred biomedical devices are ophthalmic devices, particularly contact lenses, and most particularly contact lenses made from silicone hydrogels.

As used herein, the term "ophthalmic device" refers to devices that reside in or on the eye. These devices can provide optical correction, wound care, drug delivery, diagnostic functionality or cosmetic enhancement or effect or a combination of these properties. Useful ophthalmic devices include, but are not limited to, ophthalmic lenses such as soft contact lenses, e.g., a soft, hydrogel lens; soft, non-hydrogel lens and the like, hard contact lenses, e.g., a hard, gas permeable lens material and the like, intraocular lenses, overlay lenses, ocular inserts, optical inserts and the like. As is understood by one skilled in the art, a lens is considered to be "soft" if it can be folded back upon itself without breaking.

The biomedical devices of the present invention are advantageously formed from a polymerization product of a monomeric mixture comprising (a) one or more esterified aminoalcohol monomers having one polymerizable ester-containing moiety attached to the nitrogen atom and (b) one or more biomedical device-forming comonomers. The esterified aminoalcohol monomers of component (a) are represented by the structure of Formula I:

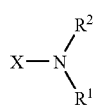
(I)

wherein X is a polymerizable ethylenically unsaturated organic ester-containing radical; $R^1$ is hydrogen, or a $C_1$-$C_{30}$ non-polymerizable hydrocarbyl group optionally substituted with a hydroxyl group including, by way of example, a substituted or unsubstituted, straight or branched $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, or a substituted or unsubstituted $C_5$-$C_{30}$ arylalkyl group, a glycerol group, an alkoxy group, an alkoxyalkyl group, a hydroxyalkoxyalkyl group, an alkylcarbonyl group, an arylcarbonyl group, and an alkylsulfonyl group, and $R^2$ is a $C_1$-$C_{30}$ non-polymerizable hydrocarbyl group substituted with a hydroxyl group. By "non-polymerizable" it is meant that the structures or substituents do not react undesirably with the biomedical device-forming comonomers or interfere undesirably with polymerization (e.g., crosslinking) of the monomers. Such non-polymerizable substituents of the esterified aminoalcohol monomers are typically non-ethylenically unsaturated radicals.

Representative examples of a "polymerizable ethylenically unsaturated organic ester-containing radical" include, by way of example, (meth)acrylate ester-containing radicals, (meth)acrylamide ester-containing radicals, vinylcarbonate ester-containing radicals, vinylcarbamate ester-containing radicals, styrene ester-containing radicals, itaconate ester-containing radicals, vinyl ester-containing radicals, vinyloxy ester-containing radicals, fumarate ester-containing radicals, maleimide ester-containing radicals, vinylsulfonyl ester-containing radicals and the like. In one embodiment, a polymerizable ethylenically unsaturated organic ester-containing radical can be represented by the general formula:

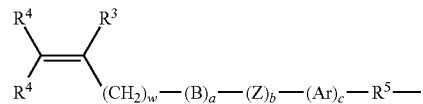

wherein $R^3$ is hydrogen or methyl; each $R^4$ is independently hydrogen, an alkyl radical having 1 to 6 carbon atoms, or a —CO—Y—$R^6$ radical wherein Y is —O—, —S— or —NH— and $R^6$ is an alkyl radical having 1 to about 10 carbon atoms; $R^5$ is an optional linking group (e.g., a divalent alkenyl radical having 1 to about 12 carbon atoms); B denotes —O— or —NH—; Z denotes —CO—, —OCO— or —COO—; Ar denotes an aromatic radical having 6 to about 30 carbon atoms; w is 0 to 6; a is 0 or 1; b is 0 or 1; and c is 0 or 1. As used herein, the term "(meth)" denotes an optional methyl substituent. Thus, terms such as "(meth)acrylate" denotes either methacrylate or acrylate, and "(meth)acrylamide" denotes either methacrylamide or acrylamide.

Representative examples of a hydroxyl-containing non-polymerizable group include, by way of example, a hydroxyl substituted $C_1$ to $C_{30}$ non-polymerizable hydrocarbyl group such as a hydroxyl substituted $C_1$ to $C_{30}$ alkyl group, preferably a hydroxyl substituted $C_1$ to $C_{16}$ alkyl group and most preferably a hydroxyl substituted $C_1$ to $C_6$ alkyl group, e.g., —$CH_2$—$CH_2$—OH or $CH_2$—CH(OH)—$CH_2$—OH; or a hydroxyl substituted alkoxyalkyl group, or a hydroxyl substituted $C_5$-$C_{30}$ aromatic group optionally containing one or more heteroatoms; or a hydroxyl substituted $C_3$-$C_{25}$ cycloalkyl group optionally containing one or more heteroatoms. In one embodiment, a hydroxyl substituted $C_5$-$C_{30}$ aromatic group can comprise one or more cyclic or polycyclic containing groups having one hydroxyl group substituted thereon.

One class of esterified aminoalcohol monomers can be represented by the structure of general Formula II:

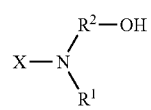
(II)

wherein X is a polymerizable ethylenically unsaturated organic ester-containing radical, $R^1$ is hydrogen, a $C_1$-$C_{30}$ non-polymerizable hydrocarbon group or an alcohol of the general formula —$R^7$OH wherein $R^7$ is a straight or branched $C_1$ to $C_{30}$ alkyl, preferably a $C_1$ to $C_{16}$ alkyl and most preferably a $C_1$ to $C_6$ alkyl, e.g., —$CH_2$—$CH_2$—OH or $CH_2$—CH(OH)—$CH_2$—OH; a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, or a substituted or unsubstituted $C_5$-$C_{30}$ arylalkyl group and $R^2$ is a straight or branched $C_1$ to $C_{30}$ alkyl, preferably a $C_1$ to $C_{16}$ alkyl and most preferably a $C_1$ to $C_6$ alkyl; a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, or a substituted or unsubstituted $C_5$-$C_{30}$ arylalkyl group. Preferably, $R^1$ is an alcohol of the general formula —$R^7$OH wherein $R^7$ is a straight or branched $C_1$ to $C_6$ alkyl and $R^2$ is a straight or branched $C_1$ to $C_6$ alkyl group.

Representative examples of alkyl groups for use herein include, by way of example, a straight or branched hydrocarbon chain radical containing carbon and hydrogen atoms of from 1 to about 30 carbon atoms, to the rest of the molecule, e.g., methyl, ethyl, n-propyl, 1-methylethyl(isopropyl), n-butyl, n-pentyl, etc., and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are defined herein, e.g., alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$R^8OR^9$, wherein $R^8$ is a bond, an alkyl, cycloalkyl or aryl group as defined herein and $R^9$ is an alkyl, cycloalkyl or aryl group as defined herein, e.g., —$CH_2CH_2OC_6H_5$ and —$CH_2CH_2OC_2H_5$, and the like.

Representative examples of cycloalkyl groups for use herein include, by way of example, a substituted or unsubstituted non-aromatic mono or multicyclic ring system of about 3 to about 30 carbon atoms such as, for example, cyclopropyl, cyclobutyl, cyclopentyl, cyclohexyl, perhydronapthyl, adamantyl and norbornyl groups bridged cyclic group or spirobicyclic groups, e.g., spiro-(4,4)-non-2-yl and the like, optionally containing one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined above directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

Representative examples of alkylcarbonyl as used herein include a group of the formula —C(=O)R wherein R is an alkyl group as defined herein and the like.

Representative examples of arylcarbonyl as used herein include a group of the formula —C(=O)R wherein R is an aryl group as defined herein and the like.

Representative examples of alkylsulfonyl as used herein include a group of the formula —S(O)$_2$R wherein R is an alkyl group as defined herein and the like.

Representative examples of ester groups for use herein include, by way of example, a carboxylic acid-containing ester and the like.

The foregoing esterified aminoalcohol monomers can be prepared by esterification techniques well known in the art. See, e.g., U.S. Pat. No. 7,078,560, the contents of which are incorporated herein. For example, the esterified aminoalcohol monomers can be prepared by esterifying an aminoalcohol-containing monomer, e.g., a monomer of the formula $R^{20}$—OH wherein $R^{20}$ is an amine-containing moiety, with a polymerizable ethylenically unsaturated organic-containing monomer.

Suitable aminoalcohols include all tertiary amines that have at least one primary alcohol function such as monoalkyldialkanolamines, dialkylmonoalkanolamines or trialkanolamines, wherein the alkyl may be a substituted or unsubstituted, linear or branched alkyl radical having $C_1$-$C_{22}$ carbon atoms and alkanol may be ethanol or propanol. Suitable monoalkyldialkanolamines include, but are not limited to, N-methyldiethanolamine, N-ethyldiethanolamine, N-methyldipropanolamine, N-ethyldipropanolamine and the like and mixtures thereof. Suitable dialkylmonoalkanolamines include, but are not limited to, dimethylaminoethanol, dimethylaminopropanol, diethylaminoethanol, diethylaminopropanol, 3-(dimethylamino)-2,2-dimethyl-1-propanol and the like and mixtures thereof. Suitable trialkanolamines include, but are not limited to, triethanolamine, tripropanolamine and the like and mixtures thereof.

Suitable polymerizable ethylenically unsaturated organic-containing monomers include, but are not limited to, $C_1$-$C_4$-alkyl(meth)acrylates such as, for example, methyl acrylate, methyl methacrylate, ethyl acrylate, isopropyl acrylate or n-butyl acrylate and the like and mixtures thereof.

Esterification can be advantageously effected at a suitable temperature, e.g., ambient temperature. Ordinarily, the reaction is carried out at substantially atmospheric pressure, although pressures above atmospheric can be employed with more volatile reactants. The reaction can be carried out in the presence of a suitable catalyst such as base catalysts, sodium methoxide, and the like. Progress of the reaction can be monitored using standard techniques such as high performance liquid chromatography (HPLC), infrared spectrometry, thin layer chromatography (TLC), Raman spectroscopy, or UV absorption. Suitable reaction conditions as well as amounts of reactants can be readily determined by one skilled in the art.

As one skilled in the art will readily appreciate, the foregoing reaction may produce a reaction mixture containing by-products such as di- or tri-polymerizable ethylenically unsaturated organic-containing amine radicals. The di- or tri-polymerizable ethylenically unsaturated organic-containing amine radical by-products will produce crosslinking in the resulting polymerization product whereas the monofunctionalized esterified aminoalcohol monomers of Formula I will produce a polymer bearing the monofunctionalized esterified aminoalcohol monomer pendant to the resulting polymeric chain. Accordingly, it may be necessary to remove the di- or tri-polymerizable ethylenically unsaturated organic-containing amine radical by-products from the resulting reaction mixture by techniques well known in the art such as chromatography to provide the esterified aminoalcohol monomers of Formula I.

In addition to the esterified aminoalcohol monomers of Formula I, the monomeric mixture will further contain at least one biomedical device-forming comonomer. In one embodiment, the biomedical device-forming comonomer is an ophthalmic device-forming comonomer such as a contact lens-forming comonomer. In a second embodiment, the biomedical device-forming comonomer is a silicone-containing monomer. Applicable silicone-containing monomeric units for use in the formation of silicone hydrogels are well known in the art and numerous examples are provided in, for example, U.S. Pat. Nos. 4,136,250; 4,153,641; 4,740,533; 5,034,461; 5,070,215; 5,260,000; 5,310,779; and 5,358,995.

Representative examples of applicable silicon-containing monomeric units include bulky polysiloxanylalkyl(meth)acrylic monomers. An example of a bulky polysiloxanylalkyl (meth)acrylic monomer is represented by the structure of Formula III:

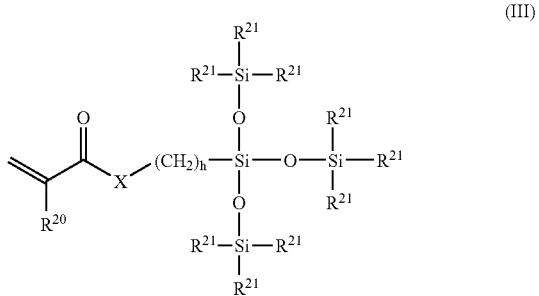

(III)

wherein X denotes —O— or —NR—; each $R^{20}$ independently denotes hydrogen or methyl; each $R^{21}$ independently denotes a lower alkyl radical, phenyl radical or a group represented by

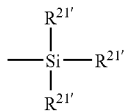

wherein each $R^{21'}$ independently denotes a lower alkyl or phenyl radical; and h is 1 to 10.

Examples of bulky monomers are 3-methacryloyloxypropyltris(trimethylsiloxy)silane or tris(trimethylsiloxy)silylpropyl methacrylate, sometimes referred to as TRIS and tris(trimethylsiloxy)silylpropyl vinyl carbamate, sometimes referred to as TRIS-VC and the like.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyldisiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety or publications, including Lai, Yu-Chin, "The Role of Bulky Polysiloxanylalkyl Methacryates in Polyurethane-Polysiloxane Hydrogels," *Journal of Applied Polymer Science*, Vol. 60, 1193-1199 (1996). PCT Published Application No. WO 96/31792 also discloses examples of such monomers, the contents of which are hereby incorporated by reference in its entirety. Further examples of silicone urethane monomers are represented by Formulae IV and V:

$$E(*D*A*D*G)_a*D*A*D*E'; \text{ or} \qquad (IV)$$

$$E(*D*G*D*A)_a*D*A*D*E'; \text{ or} \qquad (V)$$

wherein:

D denotes an alkyl diradical, an alkyl cycloalkyl diradical, a cycloalkyl diradical, an aryl diradical or an alkylaryl diradical having 6 to about 30 carbon atoms;

G denotes an alkyl diradical, a cycloalkyl diradical, an alkyl cycloalkyl diradical, an aryl diradical or an alkylaryl diradical having 1 to about 40 carbon atoms and which may contain ether or polyether, thio or amine linkages in the main chain;

\* denotes a urethane or ureido linkage;

a is at least 1;

A denotes a divalent polymeric radical of Formula VI:

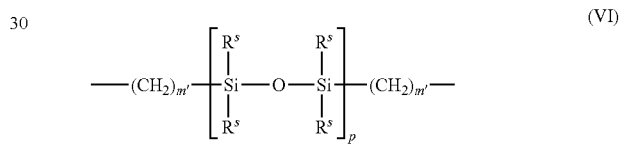

(VI)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula VII:

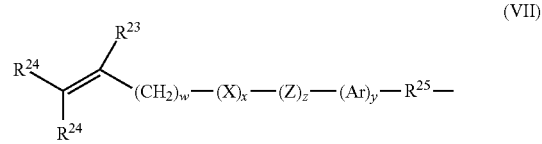

(VII)

wherein: $R^{23}$ is hydrogen or methyl;

$R^{24}$ is hydrogen, an alkyl radical having 1 to 6 carbon atoms, or a —CO—Y—$R^{26}$ radical wherein Y is —O—, —S— or —NH—;

$R^{25}$ is a divalent alkylene radical having 1 to about 10 carbon atoms;

$R^{26}$ is a alkyl radical having 1 to about 12 carbon atoms;

X denotes —CO— or —OCO—;

Z denotes —O— or —NH—;

Ar denotes an aromatic radical having about 6 to about 30 carbon atoms;

w is 0 to 6; x is 0 or 1; y is 0 or 1; and z is 0 or 1.

A preferred silicone-containing urethane monomer is represented by Formula VIII:

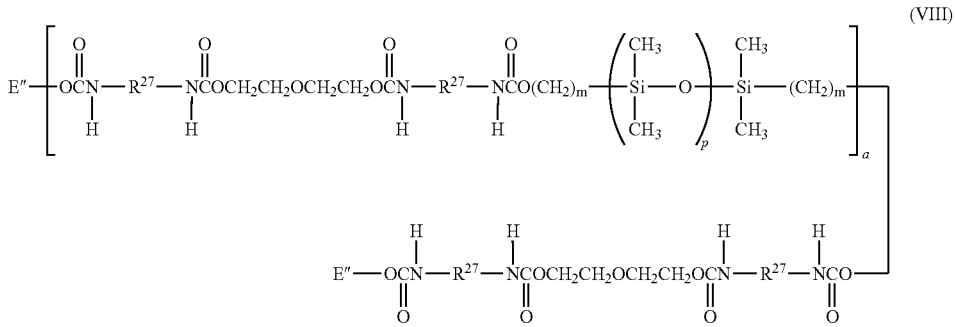

wherein m is at least 1 and is preferably 3 or 4, a is at least 1 and preferably is 1, p is a number which provides a moiety weight of about 400 to about 10,000 and is preferably at least about 30, $R^{27}$ is a diradical of a diisocyanate after removal of the isocyanate group, such as the diradical of isophorone diisocyanate, and each E" is a group represented by:

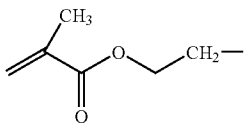

Another class of representative silicone-containing monomers includes fluorinated monomers. Such monomers have been used in the formation of fluorosilicone hydrogels to reduce the accumulation of deposits on contact lenses made therefrom, as described in, for example, U.S. Pat. Nos. 4,954, 587; 5,010,141 and 5,079,319. The use of silicone-containing monomers having certain fluorinated side groups, i.e., —($CF_2$)—H, have been found to improve compatibility between the hydrophilic and silicone-containing monomeric units, see, e.g., U.S. Pat. Nos. 5,321,108 and 5,387,662.

The above silicone materials are merely exemplary, and other materials for use in forming biomedical devices according to the present invention and have been disclosed in various publications and are being continuously developed for use in contact lenses and other medical devices can also be used. For example, an ophthalmic lens for use herein can be a cationic lens such as a cationic contact lens.

The biomedical devices of the present invention, e.g., contact lenses or intraocular lenses, can be prepared by polymerizing the foregoing monomeric mixtures to form a product that can be subsequently formed into the appropriate shape by, for example, lathing, injection molding, compression molding, cutting and the like. Alternatively, the reaction mixture may be placed in a mold and subsequently cured into the appropriate product.

For example, in producing contact lenses, the initial monomeric mixture may be polymerized in tubes to provide rod-shaped articles, which are then cut into buttons. The buttons may then be lathed into contact lenses. Alternately, the contact lenses may be cast directly in molds from the monomeric mixtures, e.g., by spincasting and static casting methods. Spincasting methods are disclosed in U.S. Pat. Nos. 3,408, 429 and 3,660,545, and static casting methods are disclosed in U.S. Pat. Nos. 4,113,224, 4,197,266, and 5,271,875. Spincasting methods involve charging the monomer mixture to a mold, and spinning the mold in a controlled manner while exposing the monomer mixture to a radiation source such as UV light. Static casting methods involve charging the monomeric mixture between two mold sections, one mold section shaped to form the anterior lens surface and the other mold section shaped to form the posterior lens surface, and curing the monomeric mixture while retained in the mold assembly to form a lens, for example, by free radical polymerization of the monomeric mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative free radical thermal polymerization initiators are organic peroxides, such as acetal peroxide, lauroyl peroxide, decanoyl peroxide, stearoyl peroxide, benzoyl peroxide, tertiarylbutyl peroxypivalate, peroxydicarbonate, and the like. Representative UV initiators are those known in the field such as, benzoin methyl ether, benzoin ethyl ether, Darocure 1173, 1164, 2273, 1116, 2959, 3331 (EM Industries) and Igracure 651 and 184 (Ciba-Geigy), and the like. Generally, the initiator will be employed in the monomeric mixture at a concentration of about 0.01 to 1 percent by weight of the total mixture.

Polymerization of the mixtures will yield a polymer, that when hydrated, forms a hydrogel. Generally, the monomeric mixture can contain the aminoalcohol monomer in an amount ranging from about 0.1 to about 99 wt. %, based on the total weight of the mixture. Optionally, a hydrophilic comonomer may be included in the initial monomeric mixture containing the aminoalcohol monomers and biomedical device-forming comonomers, for example, if it is desired to obtain a more hydrophilic copolymer. Representative hydrophilic comonomers include, but are not limited to, unsaturated carboxylic acids, such as methacrylic and acrylic acids; (meth)acrylic substituted alcohols, such as 2-hydroxyethyl methacrylate and 2-hydroxyethyl acrylate; vinyl lactams, such as N-vinylpyrrolidone; (meth)acrylamides, such as methacrylamide and N,N-dimethylacrylamide and the like and mixtures thereof.

When producing a hydrogel lens, the monomeric mixture may further include at least a diluent that is ultimately replaced with water when the polymerization product is hydrated to form a hydrogel. Generally, the water content of the hydrogel is greater than about 5 wt. % and more commonly between about 10 to about 80 wt. %. The amount of diluent used should be less than about 50 wt. % and in most cases, the diluent content will be less than about 30 wt. %. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof. If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired the monomeric mixture used to produce the hydrogel lens may further include crosslinking and wetting agents known in the prior art for making hydrogel materials.

The contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate, other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

Example 1

Preparation of
N-(2-methacryloxyethyl)diethanolamine

Triethanolamine is reacted with methyl methacrylate and sodium methoxide at ambient temperature until the unreacted mono-, di- and trimethacryloxy substituted products reached the desired distribution as determined by gas chromatography. The resulting solution is stripped of excess reagent under reduced pressure. Next, N-(2-methacryloxyethyl)diethanolamine is separated from the solution by chromatography.

Example 2

Preparation of Films from the
N-(2-methacryloxyethyl)diethanolamine of Example 1

N-(2-methacryloxyethyl)diethanolamine of Example 1 and $M_2D_{25}$ as prepared in U.S. Pat. No. 6,762,264 are dissolved in a solvent, such as hexanol, at a desired ratio, along with a minor amount of Darocur-1173 initiator. The mixture is cast between silane-treated glass plates by curing under UV light.

Example 3

Preparation of Films from the
N-(2-methacryloxyethyl)diethanolamine of Example 1

N-(2-methacryloxyethyl)diethanolamine of Example 1 and methyl methacrylate are dissolved in a solvent, at a desired ratio, along with a minor amount of Darocur-1173 initiator. The mixture is cast between silane-treated glass plates by curing under UV light.

Example 4

Preparation of Films from the
N-(2-methacryloxyethyl)diethanolamine of Example 1

N-(2-methacryloxyethyl)diethanolamine of Example 1, methacryloxypropyl tris(trimethylsiloxy)silane (TRIS) and N,N-dimethylacrylamide (DMA) are dissolved in a solvent, at a desired ratio, along with a minor amount of Darocur-1173 initiator. The mixture is cast between silane-treated glass plates by curing under UV light.

Example 5

Preparation of Films from the
N-(2-methacryloxyethyl)diethanolamine of Example 1

N-(2-methacryloxyethyl)diethanolamine of Example 1, TRIS, DMA, N-vinyl pyrrolidone (NVP) are dissolved in a solvent, at a desired ratio, along with a minor amount of Darocur-1173 initiator. The mixture is cast between silane-treated glass plates by curing under UV light.

Example 6

Preparation of Films from the N-(2-methacryloxyethyl)diethanolamine of Example 1

N-(2-methacryloxyethyl)diethanolamine of Example 1, DMA and NVP are dissolved in a solvent, at a desired ratio, along with a minor amount of Darocur-1173 initiator. The mixture is cast between silane-treated glass plates by curing under UV light.

Example 7

Preparation of Films from the N-(2-methacryloxyethyl)diethanolamine of Example 1

N-(2-methacryloxyethyl)diethanolamine of Example 1, tris(trimethylsiloxy)silylpropyl vinyl carbamate (TRIS-VC) and DMA are dissolved in a solvent, at a desired ratio, along with a minor amount of Darocur-1173 initiator. The mixture is cast between silane-treated glass plates by curing under UV light.

Example 8

Preparation of Films from the N-(2-methacryloxyethyl)diethanolamine of Example 1

N-(2-methacryloxyethyl)diethanolamine of Example 1, TRIS-VC, DMA and NVP are dissolved in a solvent, at a desired ratio, along with a minor amount of Darocur-1173 initiator. The mixture is cast between silane-treated glass plates by curing under UV light.

Example 9

Preparation of Films from the N-(2-methacryloxyethyl)diethanolamine of Example 1

N-(2-methacryloxyethyl)diethanolamine of Example 1, TRIS-dimer and DMA are dissolved in a solvent, at a desired ratio, along with a minor amount of Darocur-1173 initiator. The mixture is cast between silane-treated glass plates by curing under UV light.

Example 10

Preparation of Films from the N-(2-methacryloxyethyl)diethanolamine of Example 1

N-(2-methacryloxyethyl)diethanolamine of Example 1, TRIS-dimer, DMA and NVP are dissolved in a solvent, at a desired ratio, along with a minor amount of Darocur-1173 initiator. The mixture is cast between silane-treated glass plates by curing under UV light.

Example 11

Preparation of Contact Lenses

A monomer mixture of Example 4 is injected onto a clean polypropylene anterior mold half, the molding surface of which is shaped to provide an anterior contact lens surface, and covered with the complementary polypropylene posterior mold half, the molding surface of which is shaped to provide a posterior contact lens surface. The mold halves are compressed, and the mixture is cured by exposure to UV radiation. The top mold half is removed, and the lens is removed from the bottom mold half. After extracting residuals from the lens, the lens is hydrated in buffered saline.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A hydrogel contact lens formed from a polymerization product of a monomeric mixture comprising (a) one or more esterified aminoalcohol monomers of the general Formula I:

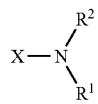

(I)

wherein X is a polymerizable ethylenically unsaturated organic ester-containing radical, $R^1$ is hydrogen, or a $C_1$-$C_{30}$ non-polymerizable hydrocarbyl group optionally substituted with a hydroxyl group, and $R^2$ is a hydroxyl-containing non-polymerizable group; and (b) one or more lens forming comonomers.

2. The contact lens of claim 1, wherein X is a vinyl ester-containing radical.

3. The contact lens of claim 1, wherein X is a (meth)acrylate ester-containing radical.

4. The contact lens of claim 1, wherein $R^2$ is a hydroxyl substituted $C_1$-$C_6$ alkyl group.

5. The contact lens of claim 1, wherein $R^1$ is an alcohol of the general formula —$R^3$OH wherein $R^3$ is a straight or branched $C_1$-$C_{30}$ alkyl group and $R^2$ is a hydroxyl substituted $C_1$-$C_6$ alkyl group.

6. The contact lens of claim 1, wherein the esterified aminoalcohol monomer is represented by the structure of general Formula II:

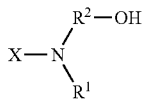 (II)

wherein X and $R^1$ have the aforestated meanings and $R^2$ is a straight or branched $C_1$-$C_6$ alkyl group, and the lens-forming comonomer is a silicone-containing monomer.

7. The contact lens of claim 6, wherein $R^1$ is an alcohol of the general formula —$R^7$OH wherein $R^7$ is a straight or branched $C_1$-$C_6$ alkyl group and $R^2$ is a $C_1$-$C_6$ alkyl group.

8. The contact lens of claim 1, wherein the lens-forming comonomer is a silicone-containing monomer.

9. The contact lens of claim 1, wherein the monomeric mixture further comprises a hydrophilic monomer.

10. The contact lens of claim 9, wherein the hydrophilic monomer includes an acrylic-containing monomer.

11. The contact lens of claim 9, wherein the hydrophilic monomer includes a vinyl-containing monomer.

12. The contact lens of claim 9, wherein the hydrophilic monomer includes at least one member selected from the group consisting of N,N-dimethylacrylamide and N-vinylpyrrolidone.

* * * * *